United States Patent
Jussel et al.

(10) Patent No.: US 11,808,520 B2
(45) Date of Patent: Nov. 7, 2023

(54) ARRANGEMENT OF A FURNACE AND OF BULK MATERIAL OF GLASS PARTICLES AS WELL AS METHOD FOR OPERATING A FURNACE

(71) Applicant: Ivoclar Vivadent AG, Schaan (LI)

(72) Inventors: Rudolf Jussel, Feldkirch-Gisingen (AT); Harald Bürke, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 715 days.

(21) Appl. No.: 16/349,743

(22) PCT Filed: Nov. 14, 2017

(86) PCT No.: PCT/EP2017/079187
§ 371 (c)(1),
(2) Date: May 14, 2019

(87) PCT Pub. No.: WO2018/091457
PCT Pub. Date: May 24, 2018

(65) Prior Publication Data
US 2020/0072552 A1     Mar. 5, 2020

(30) Foreign Application Priority Data
Nov. 15, 2016   (EP) ..................................... 16198859

(51) Int. Cl.
*A61C 13/20*     (2006.01)
*F27B 17/02*     (2006.01)
(Continued)

(52) U.S. Cl.
CPC .......... *F27B 17/025* (2013.01); *A61C 13/083* (2013.01); *A61C 13/20* (2013.01);
(Continued)

(58) Field of Classification Search
CPC ..... A61C 13/00; A61C 13/20; A61C 13/0021; A61C 13/0022; F27B 17/025; F27D 19/00; C03C 4/0021; C03B 23/0013
See application file for complete search history.

(56) References Cited

U.S. PATENT DOCUMENTS 6,303,059 B1 * 10/2001 Foser .................... F27B 17/025
                                                      264/40.1
6,484,791 B1 * 11/2002 Vidal ........................ B28B 7/34
                                                        264/16
(Continued)

FOREIGN PATENT DOCUMENTS

CA       2034893 A1     7/1991
DE    102015122861  *  10/2006
(Continued)

OTHER PUBLICATIONS

Vita Zahnfabrik, "Vita Ambria", Brochure, Germany, May 2021.

*Primary Examiner* — Gregory A Wilson
(74) *Attorney, Agent, or Firm* — Ann M. Knab; Thad McMurray

(57) ABSTRACT

The invention relates to an arrangement of a furnace and of bulk material of glass particles, said furnace (10) comprising a pressing punch (36), a pressure, distance and/or speed sensor and a control device for controlling a pressing process based on the output signal of the sensor. The sensor detects at least a pressure, position and/or motion parameter of the pressing punch (36). The pressing punch (36) acts on the bulk material of glass particles (32)—possibly via an interposed ram (28)—, said glass particles being guided and crystallizable in a press channel (30). The trigger criterion for the process control is a change of at least a motion parameter of the pressing punch (36) upon softening of the bulk material of glass particles (32) which change is detected by the sensor.

24 Claims, 3 Drawing Sheets

(51) Int. Cl.
*A61K 6/853* (2020.01)
*A61C 13/083* (2006.01)
*C03B 19/09* (2006.01)
*C03C 1/06* (2006.01)
*C03C 10/00* (2006.01)
*F27D 3/00* (2006.01)
*F27D 19/00* (2006.01)

(52) U.S. Cl.
CPC .............. *A61K 6/853* (2020.01); *C03B 19/09* (2013.01); *C03C 1/06* (2013.01); *C03C 10/00* (2013.01); *F27D 3/0033* (2013.01); *F27D 19/00* (2013.01); *F27D 2019/0003* (2013.01); *F27D 2019/0028* (2013.01); *F27D 2019/0071* (2013.01)

(56) References Cited

U.S. PATENT DOCUMENTS

| | | | |
|---|---|---|---|
| 7,290,406 B2 * | 11/2007 | Anheyer | C03B 9/41 |
| | | | 65/229 |
| 7,325,433 B2 * | 2/2008 | Foser | A61C 13/20 |
| | | | 264/16 |
| 7,691,497 B1 * | 4/2010 | Brodkin | A61C 5/77 |
| | | | 428/701 |
| 8,465,681 B2 * | 6/2013 | Jussel | A61C 13/20 |
| | | | 425/149 |
| 8,561,428 B2 * | 10/2013 | Helfenstein | C03B 9/1936 |
| | | | 65/29.15 |
| 9,022,763 B2 * | 5/2015 | Miller | A61C 13/20 |
| | | | 264/16 |
| 9,241,879 B2 * | 1/2016 | Castillo | C03B 19/02 |
| 9,745,218 B2 * | 8/2017 | Castillo | C03C 3/118 |
| 9,920,994 B2 * | 3/2018 | Jussel | F27D 21/0014 |
| 10,441,390 B2 * | 10/2019 | Jussel | F27B 17/025 |
| 10,485,640 B2 * | 11/2019 | Volkl | A61C 5/73 |
| 10,590,028 B2 * | 3/2020 | Dittmer | A61K 6/816 |
| 11,045,291 B2 * | 6/2021 | Leeson | A61C 13/083 |
| 2008/0099939 A1 | 5/2008 | Jussel | |
| 2008/0237211 A1 | 10/2008 | Jussel | |
| 2013/0302459 A1 | 11/2013 | Miller | |
| 2016/0184062 A1 | 6/2016 | Jussel | |
| 2016/0338805 A1 | 11/2016 | Jussel | |
| 2017/0128174 A1 * | 5/2017 | Mayr | A61C 13/0006 |
| 2020/0072552 A1 * | 3/2020 | Jussel | F27B 17/025 |

FOREIGN PATENT DOCUMENTS

| | | | | |
|---|---|---|---|---|
| DE | 102015122861 A1 | * | 6/2017 | ......... A61C 13/0022 |
| EP | 0438802 A1 | * | 7/1991 | |
| KR | 101347619 B1 | * | 1/2014 | |

* cited by examiner

ARRANGEMENT OF A FURNACE AND OF BULK MATERIAL OF GLASS PARTICLES AS WELL AS METHOD FOR OPERATING A FURNACE

CROSS-REFERENCE TO RELATED APPLICATIONS

This application is a National Stage application of International patent application No. PCT/EP2017/079187 filed on Nov. 14, 2107, which claims priority to European patent application No. 16198859.7 filed on Nov. 15, 2016, all the disclosures of which are incorporated herein by reference in their entirety.

FIELD OF THE INVENTION

The invention relates to an arrangement of a furnace and of bulk material of glass particles, as well as to a method of operating a furnace.

BACKGROUND OF THE INVENTION

Specific furnaces such as dental firing furnaces or dental press furnaces may be used for producing dental restorations made of, for instance, ceramics, glass or glass ceramics.

In the production of dental restorations made of glass ceramics, glass ceramic powder and/or crystallizable glass particles may be used which are inserted into a muffle in a way known per se which is placed in a firing chamber of a firing furnace or in a press chamber of a press furnace on a firing tray, preferably in a manner pre-heated in advance.

Initially, the glass ceramic powder or else the glass particles are heated until they reach a desired viscous state. Finally, during a compression process, these soft glass or glass ceramic particles are pressed using pressure to form a solid block or via the sprue channels of the muffle which are disposed among the glass or glass ceramic particles into the molding spaces for dental restoration parts, until the molding spaces are filled completely.

By means of a further debinding process and a further cooling process dental restoration parts made of, for instance, lithium silicate are provided.

However, the problem with compressing the glass particles is that crystallization occurs frequently before the glass particles are compressed completely. This uncontrolled crystallization impedes the further compression and results in a loss of strength due to a high share of remaining porosity.

Additionally, the resulting glass ceramic product is of low quality as an unfavorable crystalline structure with a broad distribution of crystal sizes occurs because of the uncontrolled crystallization.

Thus, it is desirable that complete compression of the glass particles takes place temporally before the crystallization process.

For a successful pressing process of dental glass particles it is important additionally to perform the heating process based on an exactly defined heating profile.

While, typically, the measured temperatures relate to the interior temperature of the furnace and in this respect not to the real temperature of the glass particles, a method has become known from WO 2014/131588 A1 to detect the temperature of a blank itself.

However, in case of much bulk material of glass particles there is a certain temperature gradient within the bulk material, and even using the above-mentioned favorable solution which is, however, not completely uncomplicated, the temperature of the bulk material can typically be measured at one position but not at every position.

A further problem is that with particularly configured temperature profiles the dead time of the system of muffle/glass particles delays the measured temperature profiles. It is strongly dependent on the mass of the bulk material of glass particles and of the muffle. This means that particularly voluminous muffles and much bulk material of glass particles should basically be operated in accordance with even "sharper"—that is to say longer and more exact—heating profiles.

Typically, a holding time is inserted after the heating process which is to serve the temperature equalization and in which the hot external areas of the muffle give off their heat to the center of the muffle and thus to the bulk material of glass particles.

However, this holding time prolongs the pressing cycle considerably depending on the size of the muffle, and in some cases this is not considered acceptable. Furthermore, depending on the muffle size used a corresponding control program comprising suitable temperature profiles and holding times must be selected. As the holding time is prolonged, it may not be excluded that boundary conditions which were relevant in the process in advance do have an effect on the result.

SUMMARY OF THE INVENTION

Thus, the invention is based on the task of providing an arrangement of a furnace and of bulk material of glass particles in accordance with the claims and a method of operating a furnace in accordance with the claims which ensures the quality of dental restoration parts made of glass to be produced and enables a shortened pressing cycle independent of the size of bulk material of glass particles or else of the associated muffle.

This includes the task of producing a block or blank or any other preform of glass which serves as a starting product for the production of a dental restoration.

This task is inventively solved by the independent claims. Advantageous developments may be taken from the subclaims.

According to the invention, the bulk material of glass particles is heated rapidly before it is compressed.

Depending on the material, nucleation of the crystallizable glass particles starts at the transformation range Tg (also referred to as "transformation point Tg") of the glass particles and has its maximum speed at a temperature range of approximately 50° C. above the transformation range Tg of the glass particles (Tg+50° C.) during the increase in temperature. When the temperature increases further, the speed of nucleation decreases. The speed of compression of the glass particles is increased in a temperature range of, for instance, between 50° C. above the transformation range Tg of the glass particles (Tg+50° C.) and 100° C. above the transformation range Tg of the glass particles (Tg+100° C.) when the temperature is increased.

In this connection, only few nuclei (to the desired extent) are formed according to the invention by means of a rapid heating of the glass particles from approximately the transformation range Tg of the glass particles to a temperature range of, for instance, 70° C. above the transformation range (Tg+70° C.). It is favorable that in case of a compression according to the example from the temperature range—70° C. above the transformation range Tg (Tg+70° C.)—few glass crystals are produced because of the few nuclei. This ensures that the further compression is not impeded (strongly) anymore by the undesired and uncontrolled crystallization process.

Surprisingly, this allows to determine the parameters for the compression process independent of the amount of the glass particles, the material of the glass particles and the size of the muffle.

In a preferred embodiment, it is provided that the compressed bulk material of glass particles may be cooled immediately after the compression process. As in case of a further increase in temperature—subsequent to the abovementioned example—above the "Tg+100° C." range, the speed of compression of the glass particles is decreased, while the speed of crystallization increases. In that case, crystal growth is reduced further by means of a controlled temperature or else the immediate cooling process of the glass particles after compression.

According to the invention it is particularly favorable that the inherent physical parameters of glass particles can be used as a criterion for the first time based on the invention. This represents significant progress compared to the typical and up to now widespread firing furnaces and press furnaces in which only one temperature sensor is used in the interior of the furnace. In the solution according to WO 2014/131588 A1, which is improved compared to the above-mentioned solution, at least the surface of the dental restoration part to be produced is examined. However, in particular with relatively much bulk material of dental glass particles there is a temperature gradient, and the size of the bulk material is also responsible for the temperature difference between the inside and the outside. A further disadvantage of the aforesaid solution is the need to attach additional and expensive measurement technology to the device.

Typically, a temperature gradient exists in a muffle whose isotherms extend substantially bell-shaped when viewed three-dimensionally, wherein—in terms of the bulk material of glass particles—at the bottom center of the bulk material the temperature is lowest and at the top/on the outside of the bulk material the temperature is highest. Inventively, glass particle parameters on the side faces of the bulk material are used as trigger criterion for the process control in a surprisingly subtle manner, wherein the entire softening of the glass particles is evaluated.

The process control includes the start of the pressing process, in which start the furnace temperature, the pressure in a firing chamber of the furnace and a press force of the pressing punch are controlled by the control device. Additionally, it includes the end of the pressing process or else the start of a cooling process subsequent to the pressing process, in which end or else start the press force of the pressing punch is reduced, in particular to zero, by the control device and the furnace temperature is reduced by the control device, in particular by turning off the furnace and/or opening the furnace hood.

For instance, the decrease in the speed of pressing may be used as a trigger criterion for turning off the furnace. If, in the pressing process in case of a decrease in the pressing speed, the pressing speed which is detected by the sensor amounts to a value close to zero or a value of less than 5%, in particular less than 2%, of the maximum pressing speed of the pressing punch, the criterion for turning off the furnace may be considered fulfilled, which means that the pressing process should be ended automatically or manually and the cooling process should be started.

Additionally, the counter pressure on the pressing punch because of the heating of the glass particles and the investment material in the lower part may be measured by a pressure sensor and used as a trigger criterion for the process control. For instance, the pressing process should be started when the detected counter pressure remains constant within a predefined time at a predefined level.

Furthermore, the position of the pressing punch may be detected by a position sensor and used as a trigger criterion for the process control. For instance, the furnace should be turned off when the position of the pressing punch barely changes during the pressing process within a predefined time.

Before the heating process, the inventive bulk material of glass particles made up of different starting glasses is initially filled into the press channel of the furnace and forms gradients thereat, in particular color and/or translucency gradients such that the dental restoration parts to be produced comprise the desired gradients which fit the oral situation of a patient.

The gradients correspond to at least a gradual change layer by layer and/or a continuous change of a physical property of the bulk material of glass particles.

In a further preferred embodiment, the bulk material of glass particles consists of different dyed glass particles and/or at least one type of glass which is dyed differently with pigments. Pigments include among others color pigments, opaque pigments and fluorescence pigments.

The use of pigments is particularly suitable in case of comparatively low process temperatures. In case of higher process temperatures, pigments of this type are not chemically or thermally stable in the respective glass matrix and would decompose partially or completely.

In a further preferred embodiment, the bulk material of glass particles consists of glasses having different contents of nucleating agents. After a controlled crystallization process, a block with different crystal sizes and/or different strengths in different regions may result consequently. For instance, a larger crystal size with a softer material with lower translucency in the dentine region and a fine crystalline structure having a high degree of hardness, high wear resistance and high translucency in the enamel region may be realized in a produced dental restoration.

In a further preferred embodiment, the bulk material of glass particles consists of glasses having different densities. A particularly soft, elastic region which is suitable for reproducing dentine with a small degree of hardness is possible through controlled production of residual porosity.

According to the invention, starting conditions from previous processing steps which are not ideal, such as a correct preheating temperature or preheating duration of the muffle, are also taken into account or corrected or balanced, respectively.

The bulk material of glass particles is pressurized—long before the actual pressing process takes place—by the pressing punch—typically by means of an interposed ram, for instance made of $Al_2O_3$. A force and pressure act on its upper front surface and are absorbed by its bottom side, and in some cases lead to an elastic deformation of the glass particles—if only to a (very) small extent. In any case, this force and the deformation are sufficient to make the arrangement of the glass particles which is loose after having been inserted into the muffle stronger and more stable.

Typically, the muffle mass has a comparatively low coefficient of thermal expansion of for instance $3 \times 10^{-6}$/K, while the glass particles made of, for instance, lithium silicate have a considerably higher coefficient of thermal expansion of for instance $10 \times 10^{-6}$/K. Glass particles comprise a coefficient of thermal expansion of for instance 10 or $10.5\times10^{-6}$/K until below the region that is referred to as glass transition region. In fact, the coefficient of thermal expansion rises considerably when the so-called second-order phase transition is exceeded, for instance to $14.5\times10^{-6}$/K. However, due to the softening of the glass particles particularly the shape of the glass particles is also changed. In particular, the bulk material of glass particles also starts to enter into the sprue channels for the cavities of the dental restorations as the bulk material of glass particles has become viscous by now. This presents a considerable overcompensation of the increasing coefficient of thermal expansion.

If the parameters of motion of the pressing punch are considered in this connection, micro pulses will be detected which reflect a small and short-term motion between the upper end of the bulk material of glass particles or the end which is close to the pressing punch and the muffle due to the thermal expansion of the pressing punch, the ram, the glass particles and the surrounding muffle. It is particularly favorable that in this way the temporal course of the thermal expansion may be detected as a result of the heating of the inserted system consisting of muffle, interposed ram and in particular the bulk material of the glass particles.

In a further advantageous embodiment it is provided that the control device determines the start of the pressing process independently of the temperature measured by the temperature sensor depending on the termination of the micro pulses.

In a further advantageous embodiment it is provided that the control device starts the start of the pressing process based on an increase in the measured time period between two consecutive micro pulses above a predefined threshold value.

In a further advantageous embodiment it is provided that the control device reduces the heating power to a nominal value when the time period between two consecutive micro pulses rises above a predefined, in particular second threshold value.

According to the invention, the time profile of the micro pulses is evaluated and a trigger criterion for the process control is determined either upon termination of the micro pulses of the motion parameters of the glass particles and/or upon detection of a predefined number of micro pulses and/or by evaluating the temporal distance between the micro pulses.

Thus, the invention can be used to, for instance, determine and define the ideal start of the pressing process and can thus lead the total time spent on the pressing cycle close to the optimum.

In accordance with the invention, as viewed from the motion parameters, as a trigger criterion for the actual pressing process, the occurrence of short-term micro movements is monitored and used as a criterion. It is to be understood that the micro movements are directed against the direction of pressing due to the thermal expansion of the total system of pressing punch/ram/glass particles/muffle/sheath of the firing chamber.

The pressing punch is moved to a predefined extent against the direction of pressing while the glass particles are heated, which extent amounts to in particular less than 1 mm and particularly preferable to between 0.3 and 0.5 mm.

A distance sensor or a speed sensor is primarily suitable for detecting the micro movement which is basically represented as a micro pulse of a motion parameter. The resolution should amount to at least 0.01 mm or a respective speed value, preferably 50 µm per second.

Otherwise, for instance if the press force is exerted by means of a stepping motor comprising a non-elastic or slightly elastic drive train, it is also possible to realize a power sensor or pressure sensor as a sensor for detecting the micro pulses. Alternatively, it is also possible to have a mere distance measurement, possibly at a press force of close to zero.

As a matter of course, the amplitude and frequency of the micro pulses depend on physical parameters such as the material of the glass particles to be pressed, the used investment material, the temperature, but also, for instance, the press force exerted or its regulation.

The thermal expansion counteracting the press force is substantially composed of the thermal expansion of the pressing punch, the ram, the glass particles and the muffle below the glass particles. The insulation region of the furnace below the firing chamber bottom is also heated slightly and expands correspondingly.

The fact that the pressing punch is in contact with the interposed ram and thus with the upper end of the bulk material of glass particles, preferably under contact pressure, can be used particularly favorably. The press force can be transmitted without a delay in time, as is the case with the backward motion when the material of the glass particles expands. The control device for controlling the pressing process does not only detect said expansion but also controls the further course of the temperature-time profile.

Due to the good thermal insulation the furnace is practically cold, typically between room temperature and 50° C., typically on the outside and thus at the supporting positions which are responsible for closing the furnace—at least when considered in relation to the hot firing chamber—, such that the heating existing thereat is relatively low.

In this connection, it is assumed that the heating surrounds the cylindrical firing chamber laterally in a way known per se as a ring heating and heats primarily the muffle but of course also the bulk material of glass particles located therein and possibly the ram by means of convection and thermal radiation, typically in a few minutes by several 100° C. In typical press furnaces, the wall thickness of the thermal insulation amounts to five centimeters or less and is thus within the range of the diameter of the muffle or below.

The heating in the drive train comprised of ram, pressing punch, glass particles and investment material in the lower part as well as possibly the firing tray and surrounding parts produces counter pressure acting onto the press drive.

According to the invention it is possible to use the same press force during the inventive detection of the trigger criterion as during the actual pressing process.

However, it is preferable to select an auxiliary press force of between thirty and fifty percent of the nominal press force as this is already sufficient to produce the desired motion hysteresis.

It is also possible to keep the press force at a comparatively high value for a short period of time immediately after feeding the pressing punch towards the ram—and thus indirectly towards the bulk material of glass particles—in order to ensure stable contact of the bulk material of glass particles in the muffle and to then readjust the press force.

A further aspect which is relevant for the accuracy of the measurements which have been taken is providing the negative pressure in the furnace before the measurement is taken. By means of the negative pressure in the furnace the seals between the furnace hood and the furnace bottom, or for instance between the furnace hood and an approachable firing tray, are compressed to the predefined extent. Indeed, the compression can be in a range of several millimeters and would falsify the measurement result if the negative pressure was built during the pre-pressing time, that is to say during the detection of the trigger criterion.

If—for whatever reasons—the negative pressure, as is desired during the pressing cycle, is not to be provided completely during this time, it has to be ensured at least that the negative pressure in the interior of the furnace remains constant during this pre-pressing time.

Provided that the furnace is sufficiently sealed, the negative pressure can be provided typically within a considerably shorter time than required for heating the furnace, for instance within 1 to 2 minutes.

In a further preferred embodiment it is provided that the negative pressure may be reduced by, for instance, complete or partial ventilation of the firing chamber in the pressing process if a predefined part of the bulk material of glass particles is heated and compressed. If, subsequently, another region of the glass particles is also compressed, air is trapped thereat in the gaps between the glass particles of this region which prevents complete compression of this region. This results in, for instance, a block comprising different densities.

According to a further preferred embodiment, a force control is provided for the press drive. Due to the heating process and thus during the thermal expansion of the drive train (including the bulk material of the glass particles) readjustment has to be carried out, for instance upon exceeding a predefined force. If this readjustment characteristic is adjusted correspondingly well, a number of micro pulses can be realized which is easy to be interpreted qualitatively and quantitatively. During the heating of the glass particles in a still solid physical state the distance between the micro pulses and/or the distance between intervals in which the force is readjusted increases exponentially.

As a trigger criterion an end of the micro pulse series can for instance be used, approximated by the absence of an a pulse for instance for more than 30 seconds.

However, it is possible to count the number of pulses without further ado and to determine the trigger criterion based upon this. Furthermore, it is also possible to use the amount of the time difference between two successive pulses as a trigger criterion.

In a further preferred embodiment it is provided that a crystallization program is started after the pressing process to form controlled, homogeneous glass crystals but not the undesirable crystal growth as in the compression process. As a result, for instance, a block of lithium metasilicate is produced.

Preferably, the pressing punch does not exert any pressure anymore in the crystallization program. A pressing process which is too long could lead to undesirable or inhomogeneous crystallization.

The crystallization program is preferably carried out in a temperature range between the transformation range Tg and approximately 80° C. above the transformation range Tg of the glass particles (Tg+80° C.), in particular between 40° C. above the transformation range Tg (Tg+40° C.) and approximately 60° C. above the transformation range Tg of the glass particles (Tg+60° C.). In this temperature range, nucleation of the bulk material of glass particles takes place. A subsequent increase in temperature to between 60° C. and 160° C. above Tg effects controlled crystallization. An even higher temperature for crystallization is possible but would wear out the mold unnecessarily.

In a further preferred embodiment it is provided that a cooling process and/or a demolding process is/are started after the pressing process and/or after the crystallization program. In case of a dental restoration to be produced, gypsum-based dental investment material is preferably used in a muffle, said investment material having two advantages compared to high-temperature resistant phosphate bound investment material. On the one hand, surface quality and thus reproduction accuracy is improved. On the other hand, divestment is easier.

If an ingot or a milling block is cooled and demolded directly after the pressing process, it may be checked for possible defects as it is glassy transparent then.

In a further preferred embodiment it is provided that a reusable muffle is used for a dental restoration or else dental restorations to be produced.

In a further preferred embodiment it is provided that a block of lithium silicate comprising nucleating agents is produced at the end of all processes.

Any desired heating device which provides thermal energy belongs to the furnace of the present invention.

The glass particles of the present invention refer primarily to glass powder, glass granules and glass sand, but are not limited hereto. All industrially applicable glass particles, in particular those for the production of dental restoration parts, are included in the scope of protection of the present invention.

BRIEF DESCRIPTION OF THE DRAWING

Further advantages, details and features may be taken from the following description of an exemplary embodiment of the invention in conjunction with the drawings in which.

DETAILED DESCRIPTION

Figure 1:
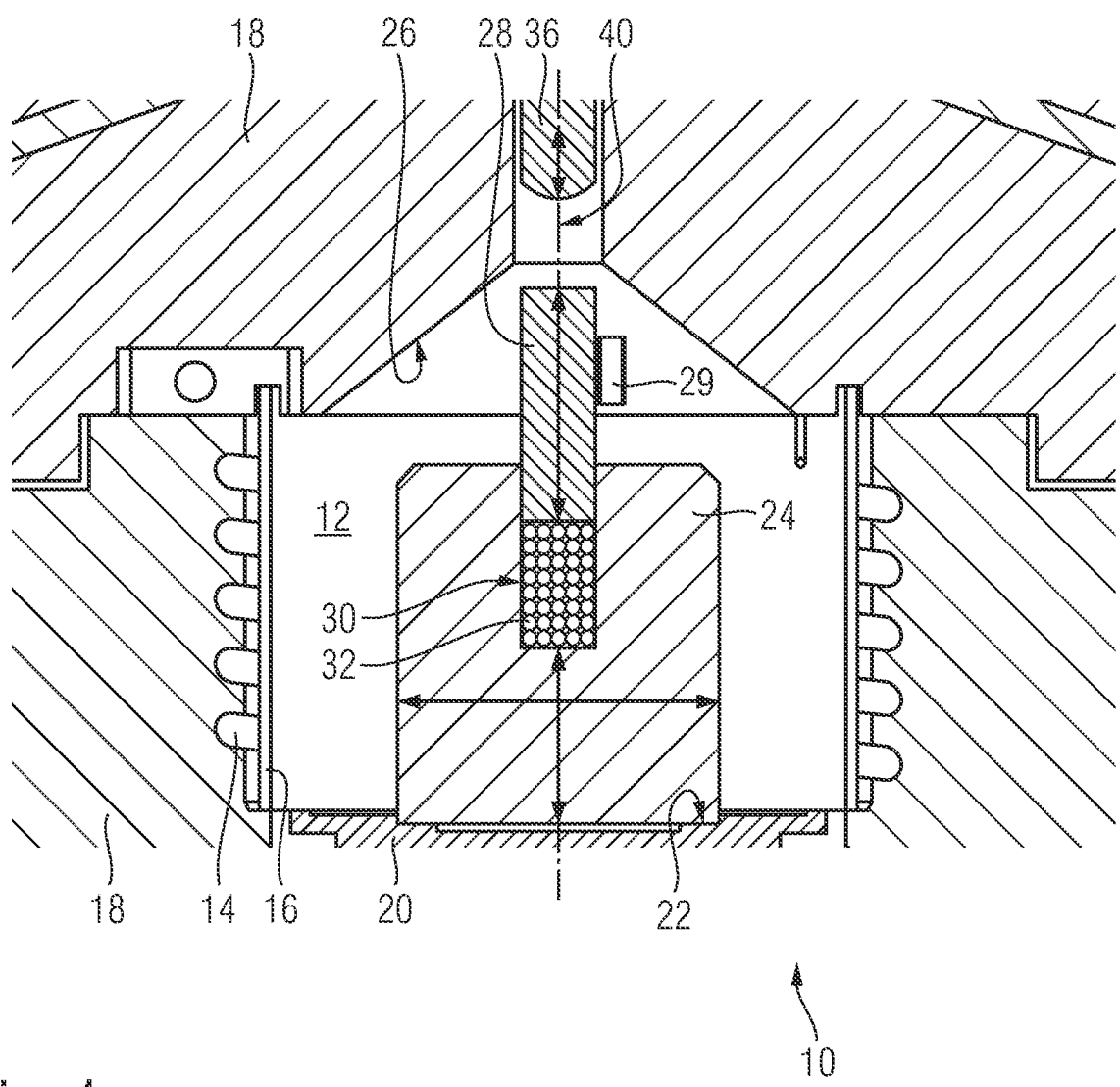
FIG. 1 shows a section through the firing chamber of an inventive furnace in one embodiment.

FIG. 1 illustrates an inventive furnace 10, which is in particular suitable for the production of dental restoration parts, showing a portion which is relevant for the invention.

A firing chamber 12 is surrounded by a heating device 14 which is illustrated schematically and comprises a helically extending heating coil which is shielded by a quartz glass 16 as a protective device. Large-volume thermal insulation elements 18 surround the firing chamber 12 on all sides, that is to say also towards the bottom, even if this is not apparent from FIG. 1.

The bottom of the firing chamber 12 is formed by a firing tray 20 which comprises recesses 22 for receiving the muffle 24, in fact graduated by different sizes, two sizes in the exemplary embodiment illustrated.

The firing chamber 12 comprises a roof cone 26 which expands the firing chamber centrally towards the top. In this area, a part of a ram 28 is received which is inserted into a press channel 30, in contact with bulk material of glass particles 32 made of lithium silicate which is received in the muffle 24 in the press channel 30 completely and which forms color and translucency gradients in the embodiment illustrated.

The ram may consist of any suitable material, for instance of $Al_2O_3$, boron nitride, graphite and/or of investment material itself.

In a pressing punch channel a pressing punch 36 is guided which is driven by a drive unit and which can exert pressure onto the ram 28 and thus indirectly onto the bulk material of glass particles 32.

In order to operate the furnace, the furnace is initially opened. A muffle which has been pre-heated, for instance, to 850° C. in a furnace referred to as a pre-heating furnace and into which cold bulk material of glass particles 32 and a cold ram 28 have already been inserted is positioned centrally on the firing tray 20. The dimensions of the recess 22 exactly match the associated muffle 24 such that the muffle 24 is positioned exactly in the center. The furnace hood is closed and a negative pressure source draws air present in the firing chamber 12 and in the thermal insulation elements until negative pressure is produced.

Seals are provided between a furnace base unit and the firing hood of the furnace which are compressed as the negative pressure becomes stronger. The negative pressure is built up within one to two minutes and is kept constant during the entire following press cycle, for instance by regulating the pressure of the negative pressure source or by continuing to run the corresponding suction pump.

As soon as the bulk material of glass particles 32 has been inserted into the muffle 24 the heating of the glass particles 32 starts which have a considerably smaller mass than the muffle 24. Because of this, the bulk material of glass particles expands wherein the pre-heating temperature is considerably below the softening temperature. The coefficient of thermal expansion of the muffle 24, that is to say of the investment material which is used for forming the muffle, is considerably smaller than the coefficient of thermal expansion of the bulk material of glass particles and of the ram and the pressing punch, wherein the pressing punch can for instance also consist of $Al_2O_3$ or for instance of steel. A sensor 29 can detect the thermal expansion of the ram of the pressing punch and added thermal expansion of the bulk material of glass particles.

In the exemplary embodiment illustrated herein, the coefficient of thermal expansion of the muffle is $3\times10^{-6}$/K and of the respective glass particles is approximately $10\times10^{-6}$/K, and that of the pressing punch is $8\times10^{-6}$/K.

In the thermal expansion in axial direction considered herein, the thermal expansions $L_0$ sum up during the heating. The total thermal expansion $L_{0\ tot}$ is:

$$L_{0\ tot} = L_{0\ IVM} + L_{0\ bulk\ material\ of\ glass\ particles} + L_{0\ Alox\ ram} + L_{0\ pressing\ punch}$$

In this connection, the pressing punch 36 only needs to be taken into account in as much as it is heated, that is to say in the region of the thermal insulation elements 18 adjacent to the firing chamber.

The opposite end of the pressing punch 36 which is connected to the drive unit is considerably less hot, for instance under 100° C.

The temperature gradient of the pressing punch 36 is high in particular if a pressing punch for instance made of $Al_2O_3$ is used; if a metallic pressing punch is used, an additional thermal insulation cylinder may be integrated into the pressing punch.

$L_{0\ IVM}$ is the axial length of the muffle or investment material below the press channel 30.

In the illustrated embodiment of the furnace the firing tray 20 is only warm on its surface and already comparatively cool in the lower region. However, this does not hold true if a heating referred to as a base heating of a firing chamber is realized, that is to say if a further heating is provided below the firing tray 20. In this embodiment the additional thermal expansion in the region thereat needs to be added to the above-mentioned total thermal expansion.

In order to identify the axial displacement of the pressing punch 36 as a consequence of the thermal expansion, the thermal expansion of the furnace itself upon heating needs to be deducted from $L_{0\ tot}$. However, in this connection it must be taken into account that the sealing and the closing force of the furnace are typically realized far to the outside and that the thermal expansion thereat is typically limited to a range between room temperature and a temperature below 100° C., for instance 60° C.; the thermal insulation elements 18 that become very hot at least on the inside do not exert any axial forces but are supported easily in the furnace.

Here, axial refers to the axis 40 of the pressing punch 36 which runs centrally through both the ram and the bulk material of glass particles 32 as well as through the muffle 24 and the firing tray 20; all elements are configured circular symmetrically in the exemplary embodiment illustrated.

Figure 2:
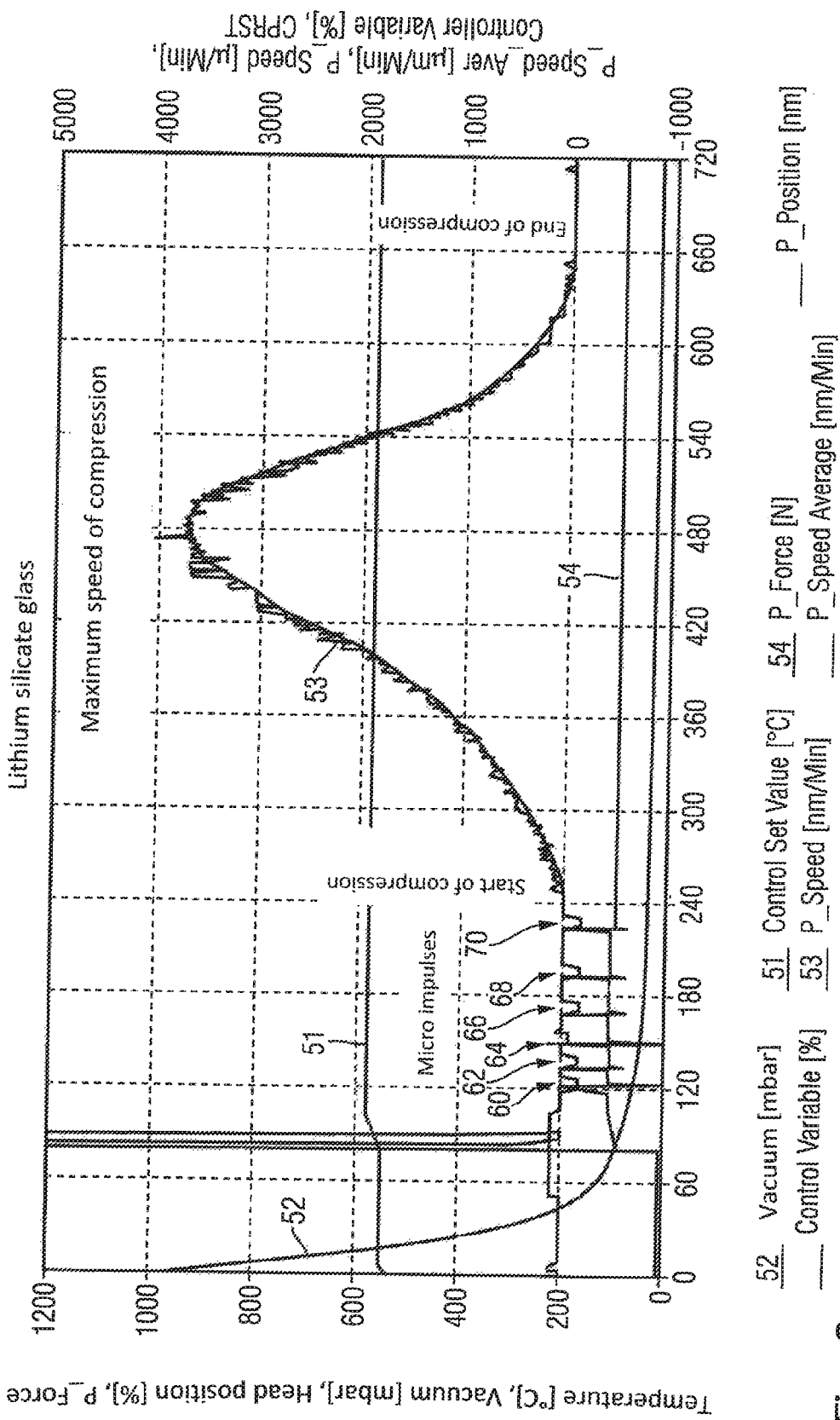
FIG. 2 shows a diagram illustrating the speed of the pressing punch and further physical quantities, plotted over time.

In FIG. 2 a plurality of curves are plotted in the same diagram and the axis of abscissas is time. Here, the following values are concerned:

The temperature curve 51 shows the regulated temperature in the firing chamber of the furnace.

The pressure curve 52 shows the pressure in the interior of the furnace.

The speed curve 53 shows the speed of the pressing punch 36 or of the associated drive unit.

Here, the neutral point of the ordinate is vertically offset and the speed values in μm/min are recorded on the right hand side.

The applied press force is recorded in the press force curve 54.

As can be seen from FIG. 2, the furnace 10 has already been pre-heated to approximately 550° C. at the considered beginning. The heating continues working. At the point in time of approximately 70 seconds from the start heating is carried out, wherein the target temperature is at approximately 580° C. in the exemplary embodiment illustrated. After 10 seconds, at approximately 80 seconds, the peak of the speed thereat is used to insert the pressing punch 36 rapidly into the press channel 30, until pressing punch, ram and the bulk material of glass particles are in contact with one another. The pressing punch 36 exerts a constant pressure of approximately 100 N onto the bulk material of glass particles 32.

As can be seen from the pressure curve 52, the pressure in the furnace drops rapidly within the first 40 seconds and amounts to 100 mbar at 70 seconds. At 240 seconds at the latest, the final pressure of 50 mbar is reached. This pressure is kept constant during the entire press cycle.

From 70 seconds to approximately 115 seconds the speed of the pressing punch 36 amounts to 0, as can be seen from FIG. 2. At slightly more than 115 seconds an inventive micro pulse 60 at a negative speed is produced. This micro pulse 60 corresponds to a thermal expansion $L_{0\ tot}$, as has been explained with regard to FIG. 1. The micro pulse has a height of approximately 500 μm/min and a duration of less than one second, depending on the quality of the press force regulation—even if this is not clearly evident from FIG. 2, based on the embodiment illustrated herein.

The upper end of the bulk material of glass particles 32 automatically slides upwards slightly, contrary to the force of the press power according to the press curve 54, and drops again within a short period of time due to the softening of the glass particles. At the point in time of approximately 135 seconds, the next micro pulse 62 is produced. Further micro pulses 64, 66, 68 and 70 follow at 150, 170, 195 and 225 seconds, while the following period of time until 250 seconds remains free of micro pulses.

In the exemplary embodiment illustrated, the pressing process is triggered inventively through detection of a number of micro pulses predefined by experience when the number of micro pulses according to FIG. 2 reaches six.

According to the invention, this means that the glass particles 32 have become micro-plastic or viscous; the further thermal expansion occurs without pulses. According to the invention, this fact is judged as an indication that the bulk material of glass particles has reached the actual desired temperature for preparing the pressing process.

For detecting the micro pulses it is basically possible to carry out a speed detection, a distance detection or a press force detection, depending on the resolution of the available sensors and depending on the elasticity of the drive. In tests in connection with the exemplary embodiment discussed herein, a speed detection has proven to be the most advantageous detection, whereas a distance detection is basically also possible.

Although the entire heating time of the bulk material of glass particles until the beginning of the compression is not apparent from FIG. 2, it has to be noted that a considerably faster heating process is carried out inventively compared to the prior art. As a result, a controlled, small amount of nuclei is produced.

The compression process starts at 250 seconds until approximately 660 seconds. Meanwhile, the compression reaches its maximum speed at approximately 470 seconds.

In a preferred embodiment it is provided that a cooling program is started immediately after the compression process to avoid the crystal growth which would take place otherwise at a higher temperature.

In a further preferred embodiment it is provided that a crystallization program is started after the compression process such that a desired, homogenous and finer crystal structure is produced.

In a further preferred embodiment it is provided that a cooling program and/or a crystallization program and/or a demolding program and/or a cleaning program is carried out after the compression process. As a result, for instance, a block of lithium metasilicate glass ceramic or of lithium silicate glass with nucleating agents is produced.

Figure 3:
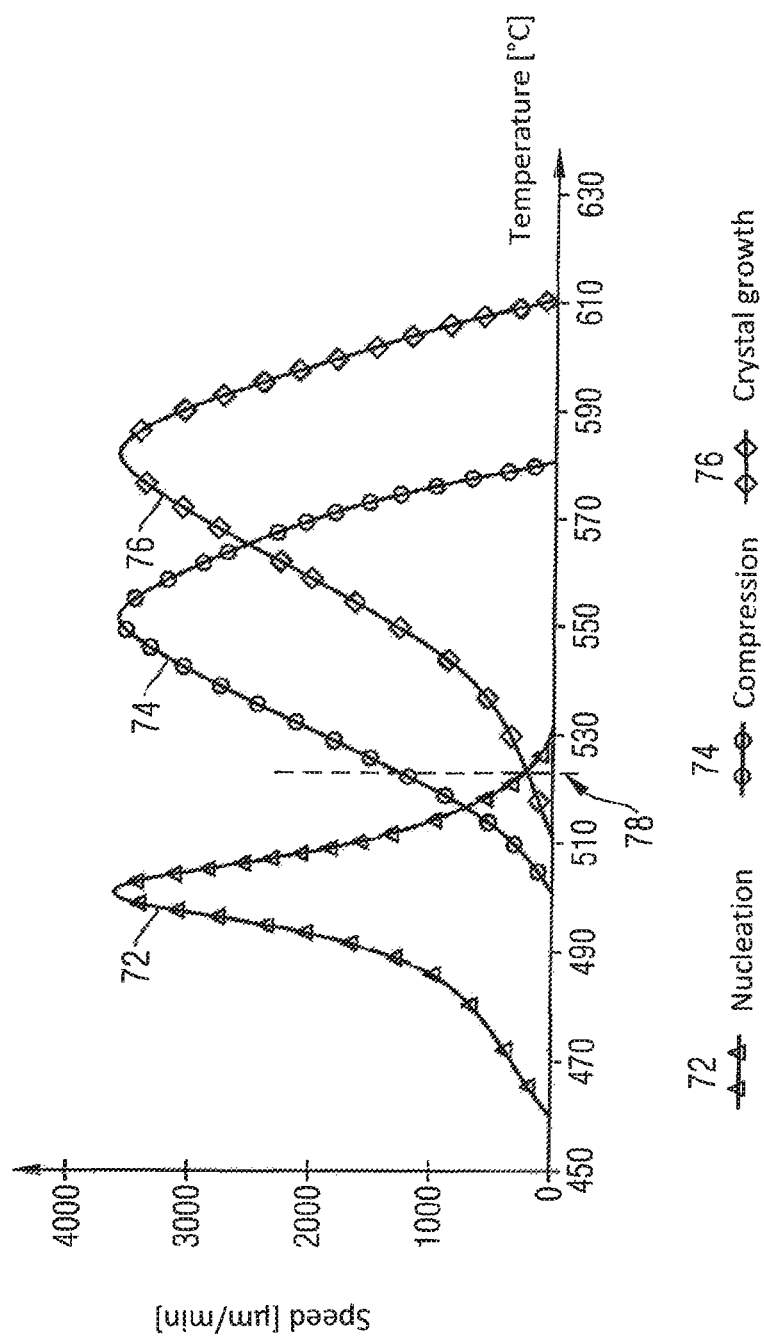
FIG. 3 shows a schematically illustrated diagram of the speed of nucleation, compression and crystal growth, plotted over temperature.

In FIG. 3, three curves 72, 74, 76 are recorded in a diagram wherein the axis of abscissas is the temperature. The speed curves 72, 74, 76, each comprising a plurality of triangles, circles and squares to differentiate them from one another, show the speed of nucleation, of compression and of crystal growth of the glass particles made of lithium silicate under different temperatures.

Here, the neutral point of the axis of abscissas—that is to say of the temperature—is vertically offset and corresponds to the transformation range Tg of glasses made of lithium silicate which amounts to approximately 450° C. In the transformation range Tg the viscosity n of the glass particles made of lithium silicate amounts to approximately 10exp13.2 Poise and the micro pulses have already ended as long as the thermal expansion of the bulk material of glass particles is compensated by micro-plastic deformation at the positions of contact of the glass particles and the viscosity n reaches a height of 10exp14.5 Poise.

It is apparent from FIG. 3 that nucleation of glasses made of lithium silicate takes place in the temperature range between 460 and 530° C., that is to say between 10° C. above the transformation range Tg of the glass particles (Tg+10° C.) and 80° C. above the transformation range Tg of the glass particles (Tg+80° C.), compression thereof takes place in the temperature range between 500 and 580° C., that is to say between 50° C. above the transformation range Tg of the glass particles (Tg+50° C.) and 130° C. above the transformation range Tg of the glass particles (Tg+130° C.), crystal growth thereof takes place in the temperature range between 510 and 610° C., that is to say between approximately 60° C. above the transformation range Tg of the glass particles (Tg+60° C.) and 160° C. above the transformation range Tg of the glass particles (Tg+160° C.).

These three temperature ranges overlap one another, and in these temperature ranges there is a maximum speed of nucleation (at approximately 500° C.), a maximum speed of compression (at approximately 550° C.) and a maximum speed of crystal growth (at approximately 580° C.), respectively.

To form only few nuclei (to a desired extent) before and during the compression process, to ensure that complete compression is not prevented strongly by the nuclei, rapid heating is carried out inventively, for instance within three minutes, from 460° C. (Tg+10° C.) to 520° C. (Tg+70° C.) in accordance with the temperature point 78 according to FIG. 3.

At the temperature point 78, both nucleation and crystal growth have a relatively small speed, while the speed of compression is relatively large. Thus, this temperature point 78 is utilized according to the invention. If a rapid heating process to the temperature point 78 is carried out, as few nuclei and glass crystals as possible are formed before and during compression.

Except for the optimum temperature point 78, the end temperature for the rapid heating process may be another predefined temperature of between 500° C. (Tg+50° C.) and 530° C. (Tg+80° C.) which at least corresponds to the dilatometric softening of the glass particles and at which the viscosity of the glass particles η? amounts to at least 10exp11.5 Poise.

References to "process control" or "control device" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices.

The control device may be implemented as one or more central processing unit (CPU) chips, logic units, cores (e.g. as a multi-core processor), field-programmable gate arrays (FPGAs), application specific integrated circuits (ASICs), or digital signal processors (DSPs).

References to sensors can be understood to include, but are not limited to, any known sensor such as transducers, optical sensors such as ir, uv, photo detectors, photodiodes, phototransistors; motion, inertia and position measurement sensors such as accelerometers, gyroscopes, force, tilt, vibration, flow, float level sensors; capacitive touch/proximity sensors, ultrasonic receivers, transmitters, image sensors, cameras, magnetic sensors; pressure sensors such as absolute, sealed gauge, compound, switch, differential, vacuum and vented gauge sensors.

The invention claimed is:

1. An arrangement of a furnace and of bulk material of glass particles comprising
a furnace, and
bulk material of glass particles,
wherein said furnace comprises
a muffle,
a pressing punch, a pressure, distance and/or speed sensor and
a process controller configured for controlling a pressing process based on an output signal of the sensor,
wherein the sensor detects at least a pressure, position and/or motion parameter of the pressing punch,
wherein the pressing punch acts on the bulk material of glass particles,
wherein said glass particles are guided and crystallizable in a press channel,
wherein trigger criterion for the process controller is a change of at least a motion parameter of the pressing punch upon softening of the bulk material of glass particles which change is detected by the sensor,
wherein the sensor, below the softening temperature of the bulk material of glass particles, detects the thermal expansion of the muffle, a ram of the pressing punch, and the bulk material of glass particles, said thermal expansion counteracting the press force.

2. The arrangement of a furnace and of bulk material of glass particles as claimed in claim 1,
wherein the process controller controls the start of the pressing process, in which start the furnace temperature, the pressure in a firing chamber of the furnace and a press force of the pressing punch are controlled by the process controller, and
wherein the process controller controls the end of the pressing process, in which end the press force of the pressing punch is reduced by the process controller, and the furnace temperature is reduced by the process controller.

3. The arrangement of a furnace and of bulk material of glass particles as claimed in claim 2,
wherein the press force of the pressing punch is reduced by the process controller to zero and the furnace temperature is reduced by the process controller by turning off the furnace (10).

4. The arrangement of a furnace and of bulk material of glass particles as claimed in claim 1,
wherein the bulk material of glass particles forms gradients, in the press channel.

5. The arrangement of a furnace and of bulk material of glass particles as claimed in claim 4,
wherein the gradients formed comprise color and/or translucency gradients.

6. The arrangement of a furnace and of bulk material of glass particles as claimed in claim 4,
wherein the gradients correspond to at least a gradual change layer by layer and/or a continuous change of a physical property of the bulk material of glass particles.

7. The arrangement of a furnace and of bulk material of glass particles as claimed in claim 1,
wherein the bulk material of glass particles comprises different dyed glass particles and/or at least one glass type which is dyed differently with pigments, and/or glass with different contents of nucleating agents and/or with different densities.

8. The arrangement of a furnace and of bulk material of glass particles as claimed in claim 1,
wherein the at least one motion parameter comprises micro pulses and wherein a start of the pressing process is the termination of micro pulses of the motion parameter and/or the number thereof and/or the temporal distance thereof.

9. The arrangement of a furnace and of bulk material of glass particles as claimed in claim 8,
wherein the micro pulses reflect a short-term and small motion between the bulk material of glass particles and the muffle.

10. The arrangement of a furnace and of bulk material of glass particles as claimed in claim 8,
wherein the process controller detects a number of micro pulses of the motion parameter and/or a distance between the micro pulses and/or a change in distance between the micro pulses and/or a size of the micro pulses and uses one or more detected criterion for the process controller.

11. The arrangement of a furnace and of bulk material of glass particles as claimed in claim 1,
wherein the trigger criterion for an end of the pressing process is a decrease of pressing speed to a value close to zero or a value of less than 5% or a value of less than 2% of maximum pressing speed of the pressing punch.

12. The arrangement of a furnace and of bulk material of glass particles as claimed in claim 1,
wherein the process controller detects a backward motion of the pressing punch in correspondence with the thermal expansion of the bulk material of glass particles via the sensor, and
wherein the trigger criterion for the process controller to start the pressing process is an end of the backward motion and/or the beginning of a forward motion and/or a defined point in time after a change of motion parameters of the pressing punch.

13. The arrangement of a furnace and of bulk material of glass particles as claimed in claim 1,
wherein the sensor supplies the decreasing counterforce which corresponds to the softening of the bulk material of glass particles due to thermal expansion coefficients or due to differences between thermal expansion coefficients to the process controller,
wherein the process controller sets a further process sequence to a point in time after detection of the softening of the bulk material of glass particles.

14. The arrangement of a furnace and of bulk material of glass particles as claimed in claim 1,
wherein the process controller brings the pressing punch into contact with the bulk material of glass particles before the actual pressing process and detects the thermal expansion of the bulk material of glass particles corresponding to a motion of the pressing punch against the direction of pressing and uses the decreasing counterforce if no further thermal expansion takes place or upon softening.

15. The arrangement of a furnace and of bulk material of glass particles as claimed in claim 1,
wherein the process controller causes the pressing punch to exert a press force or a press power onto the bulk material of glass particles before the bulk material of glass particles has softened.

16. The arrangement of a furnace and of bulk material of glass particles as claimed in claim 1,
wherein based on the motion parameter detected by the sensor, the press power exerted by the pressing punch and/or the temperature of a temperature sensor disposed in or at the firing chamber, the process controller identifies the type and the material of the bulk material of glass particles based on predefined signatures and controls the pressing process.

17. The arrangement of a furnace and of bulk material of glass particles as claimed in claim 1,
wherein during the detection of the motion parameter the pressing punch exerts a constant force or a force which follows a predefined profile onto the bulk material of glass particles and the motion parameter is detected after the pressing punch has been brought into contact with the bulk material of glass particles.

18. The arrangement of a furnace and of bulk material of glass particles as claimed in claim 1,
wherein the pressing punch is moved to a predefined extent during the heating of the bulk material of glass particles.

19. A method for operating a furnace comprising a muffle, a pressing punch, a pressure, distance and/or speed sensor and a process controller for controlling a pressing process comprising,
detecting, with the pressure, distance and/or speed sensor, at least a pressure, position and/or motion parameter of the pressing punch,
controlling, with the process controller, the pressing process based on an output signal of the sensor,
wherein, in the pressing process, the pressing punch acts on bulk material of glass particles and exerts pressure thereon,
said bulk material of glass particles being introduced in a press channel of a muffle,
wherein trigger criterion for the process controller is a change of at least a motion parameter of the pressing punch corresponding to the softening of the bulk material of glass particles, which change is detected by the sensor,
wherein the sensor, below the softening temperature of the bulk material of glass particles, detects the thermal expansion of the muffle, a ram of the pressing punch, and the bulk material of glass particles, said thermal expansion counteracting the press force.

20. The method as claimed in claim 19,
wherein the at least a motion parameter comprises micro pulses,
wherein after the termination of micro pulses of the motion parameter the bulk material of glass particles is heated to a predefined temperature, which corresponds to at least the dilatometric softening of the bulk material of glass particles, within ten minutes.

21. The method as claimed in claim 19,
wherein, after the pressing process, a crystallization program is started in which the pressing punch exerts no pressure anymore.

22. The method as claimed in claim 19,
wherein nucleation of the bulk material of glass particles takes place in the temperature range between the transformation range or transformation point Tg of the bulk material of glass particles and 100° C. above the transformation range Tg (Tg+100° C.).

23. The method as claimed in claim 19,
wherein after the pressing process and/or after a crystallization program, a cooling process and/or a demolding process is/are started.

24. The method as claimed in claim 19,
wherein at the end of the method a block made of lithium metasilicate and/or of lithium silicate with nucleating agents is formed.

* * * * *